United States Patent
Romanovsky

(10) Patent No.: US 12,257,216 B2
(45) Date of Patent: Mar. 25, 2025

(54) TREATMENT FOR HOT FLUSHES

(71) Applicant: Dignity Health, San Francisco, CA (US)

(72) Inventor: Andrej A. Romanovsky, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 32 days.

(21) Appl. No.: 18/046,876

(22) Filed: Oct. 14, 2022

(65) Prior Publication Data

US 2023/0135909 A1    May 4, 2023

Related U.S. Application Data

(63) Continuation of application No. 16/628,208, filed as application No. PCT/US2018/040902 on Jul. 5, 2018, now abandoned.

(Continued)

(51) Int. Cl.
*A61K 31/17*     (2006.01)
*A61K 9/00*      (2006.01)
(Continued)

(52) U.S. Cl.
CPC ............ *A61K 31/17* (2013.01); *A61K 9/0014* (2013.01); *A61K 31/167* (2013.01);
(Continued)

(58) Field of Classification Search
CPC ...... A61K 31/167; A61K 31/17; A61K 31/18; A61K 31/4725; A61K 31/55; A61K 9/0014; A61K 45/06
See application file for complete search history.

(56) References Cited

U.S. PATENT DOCUMENTS

2009/0258040 A1    10/2009   Monti
2010/0137360 A1    6/2010    Gomtsyan et al.
(Continued)

FOREIGN PATENT DOCUMENTS

JP    2012505907 A    3/2012
JP    2020526507 A    8/2020
(Continued)

OTHER PUBLICATIONS

Gunthorpe et. al., Neuropharmacology, vol. 46, pp. 133-149, publ. 2004 (Year: 2004).*

(Continued)

*Primary Examiner* — Sarah Pihonak
(74) *Attorney, Agent, or Firm* — Polsinelli PC

(57) ABSTRACT

Disclosed herein are methods for treating hot flushes in a subject. In one embodiment, treating hot flushes includes administering to a subject in need of such treatment, a therapeutically effective amount of a transient receptor potential channel (TRP channel) blocker or a pharmaceutically acceptable salt thereof. Also disclosed herein are methods for amelioration, alleviation, or prevention of the thermal discomfort in hot flushes, comprising: selecting a subject in need of treatment for hot flushes, administering to the subject a therapeutically effective amount of a TRP channel blocker, such as a TRPV1 blocker, or a pharmaceutically acceptable salt thereof.

17 Claims, 7 Drawing Sheets

| COMPOUND | COMPANY |
|---|---|
| V120083 | Purdue Pharma |
| ABT-102 | Abbott Laboratories/AbbVie |
| ABT-443 | Abbott Laboratories/AbbVie |
| AZD-1386 | AstraZeneca |
| PHE-337 | PharmEste |

Related U.S. Application Data

(60) Provisional application No. 62/529,269, filed on Jul. 6, 2017.

(51) Int. Cl.
  *A61K 31/167* (2006.01)
  *A61K 31/4725* (2006.01)
  *A61K 31/55* (2006.01)
  *A61K 45/06* (2006.01)

(52) U.S. Cl.
  CPC .......... *A61K 31/4725* (2013.01); *A61K 31/55* (2013.01); *A61K 45/06* (2013.01)

(56) References Cited

U.S. PATENT DOCUMENTS

| | | | |
|---|---|---|---|
| 2015/0352123 A1 | 12/2015 | Gonzales | |
| 2020/0147014 A1 | 5/2020 | Romanovsky | |

FOREIGN PATENT DOCUMENTS

| | | | | |
|---|---|---|---|---|
| WO | WO-2005006881 A2 * | 1/2005 | ......... | A23L 1/22091 |
| WO | 2009073788 A1 | 6/2009 | | |
| WO | WO-2010045401 A1 * | 4/2010 | .......... | C07D 311/74 |
| WO | 2014089067 A2 | 6/2014 | | |
| WO | 2017112693 A1 | 6/2017 | | |

OTHER PUBLICATIONS

Voight, E. A. et al., "Discovery of (R)-1-(7-Chloro-2,2-bis(fluoromethyl)chroman-4-yl)-3-(3-methylisoquinolin-5-yl)urea (A-1165442): A Temperature-Neutral Transient Receptor Potential Vanilloid-1 (TRPV1) Antagonist with Analgesic Efficacy", Journal of Medicinal Chemistry, vol. 57, Jun. 16, 2014, pp. 7412-7424.
Reilly R. M. et al., "Pharmacology of Modality-Specific Transient Receptor Potential Vanniloid-1 Antagonists that Do Not Alter Body Temperature", Journal Pharmacology and Experimental Therapeutics, May 7, 2012, vol. 342, No. 2, pp. 416-428.
Kanai Y. et al., "Differential involvement of TRPV1 receptors at the central and peripheral nerves in CFA-induced mechanical and thermal hyperalgesia", Journal of Pharmacy and Pharmacology, Jan. 29, 2007, vol. 59, No. 5, pp. 733-738.
Uchytilova E. et al., "TRPV1 antagonist attenuates postoperative hypersensitivity by central and peripheral mechanisms", Molecular Pain, Nov. 17, 2014, vol. 10, No. 67, pp. 1-13.
IP Australia, Examination Report No. 1, Application No. 2018297270 Jun. 23, 2023, 11 pages.
Japan Patent Office, Notice of Reasons for Rejection, Application No. 2019-572733, Aug. 8, 2022, 10 pages.
Ohnuki, K. et al., "CH-19 Sweet, Nonpungent Cultivar of Red Pepper, Increased Body Temperature in Mice with Vanilloid Receptors Stimulation by Capsiate," Journal Nutri Sci Vitaminol, vol. 47, pp. 295-298.
Vriens, J. et al., "Pharmacology of Vanilloid Transient Receptor Potential Cation Channels," Molecular Pharmacology vol. 75, Jun. 2009, pp. 1262-1279.
Gomtsyan, A. et al., "Identification of (R)-1-(5-tert-Butyl-2,3-dihydro-1Hinden-1-yl)-3-(1H-Indazol-4-yl)urea (ABT-102)as a Potent TRPV1 Antagonist for Pain Management," Journal Medicinal Chemistry 51(3), Jan. 10, 2008, pp. 392-395.
Garami, A. et al., "Contributions of Different Modes of TRPV1 Activation to TRPV1 Antagonist-Induced Hyperthermia," Journal of Neuroscience vol. 30(4), Jan. 27, 2010, pp. 1435-1440.
Patent Cooperation Treaty, International Search Report and Written Opinion, International Application No. PCT/US2018/040902, date of mailing Aug. 31, 2018, 3 pages.
Korean Intellectual Property Office, Notice of Preliminary Rejection, Korean Patent Application No. 10-2020-7003542, Jun. 20, 2023, 18 pages.
Gavva, N. R. et al. "Proton Activation Does Not Alter Antagonist Interaction with the Capsaicin-Binding Pocket of TRPV1," Molecular Pharmacology vol. 68, No. 6, Aug. 30, 2005, pp. 1524-1532.
Doherty, E. M. et al. "Novel Vanilloid Receptor-1 Antagonist: 2. Structure—Activity Relationships of 4-Oxopyrimidines Leading to the Selection of a Clinical Candidate," J. Med. Chem., Jun. 22, 2007, pp. 3515-3527.
Tojo, S. et al. "Crystal Structures and Structure—Activity Relationships of Imidazothiazole Derivatives as IDO1 Inhibitors," ACS Medicinal Chemistry Letters vol. 5, Aug. 21, 2014, pp. 1119-1123.
European Patent Office, Communication Pursuant to Article 94(3) EPC, Application No. 18828376.6, Jan. 8, 2024, 9 pages.
Korean Intellectual Property Office, Notice of Preliminary Rejection, Application No. 10-2024-7000103, Feb. 17, 2024, 12 pages.
Japan Patent Office, Notice of Reasons for Rejection, Application No. 2023-092285, Aug. 6, 2024, 9 page.
Canadian Intellectual Property Office, Examiner's Report, Application No. 3,068,590, Aug. 14, 2024, 5 pages.

* cited by examiner

Figure 5

| COMPOUND | COMPANY |
|---|---|
| A-425619 | Abbott Laboratories/AbbVie |
| A-889425 | Abbott Laboratories/AbbVie |
| A-1165442 | Abbott Laboratories/AbbVie |
| A-784168 | Abbott Laboratories/AbbVie |
| A-995662 | Abbott Laboratories/AbbVie |
| ABT-102 | Abbott Laboratories/AbbVie |
| ABT-116 | Abbott Laboratories/AbbVie |
| ABT-443 | Abbott Laboratories/AbbVie |
| AMG0347 | Amgen |
| AMG517 | Amgen |
| AMG628 | Amgen |
| AMG1629 | Amgen |
| AMG2820 | Amgen |
| AMG3731 | Amgen |
| AMG7905 | Amgen |
| AMG7988 | Amgen |
| AMG8163 | Amgen |
| AMG8562 | Amgen |
| AMG8563 | Amgen |
| AMG9810 | Amgen |
| AMG986 | Amgen |
| PAC-14028 | AmorePacific |
| AS1928370 | Astellas Pharma |
| AZD-1386 | AstraZeneca |
| DWP-05195 | Daewoong Pharmeutical |
| MCS-18 | DoNatur |
| SB-366791 | GSK |
| SB-705498 | GSK |
| SB-782443 | GSK |
| SB-452533 | GSK |
| JNJ-17203212 | J&J |
| JNJ-38893777 | J&J |
| JNJ-39439335 (Mavatrep) | J&J |
| JNJ-39729209 | J&J |
| JTS-653 | Japan Tobacco |
| KYS-05090 | Kyung Hee University |
| GRC-6211 | Lilly-Glenmark |
| GRC-6127 | Lilly-Glenmark |
| MK-2295 | Merck-Neurogen |
| NGD-8243 | Merck-Neurogen |

Figure 5 continued

| COMPOUND | COMPANY |
|---|---|
| MR-1817 | Mochida Pharmaceutical |
| NEO-6860 | NeoMed Institute |
| BCTC | Neurogen |
| KJM429 | NIH |
| Phe377 | PharmEste |
| Phe575 | PharmEste |
| V116517 | Purdue Pharma |
| V120083 | Purdue Pharma |
| Capsazepine | Sandoz (Novartis) |
| SAR-115740 | Sanofi-Aventis |
| JYL1421 | Schwartz Pharma |
| WL-1001 | Winston Laboratories |
| WL-1002 | Winston Laboratories |
| M68008 | Wyeth-Mochida |
| XEN-D0501 | (Xention, Ario Pharmo) Pila Pharma |
| A-1165901 | Abbott Laboratories/AbbVie |

Figure 6

| COMPOUND | COMPANY |
|---|---|
| V120083 | Purdue Pharma |
| ABT-102 | Abbott Laboratories/AbbVie |
| ABT-443 | Abbott Laboratories/AbbVie |
| AZD-1386 | AstraZeneca |
| PHE-337 | PharmEste |

TREATMENT FOR HOT FLUSHES

CROSS-REFERENCE TO RELATED APPLICATIONS

This application is a continuation that claims benefit to U.S. application Ser. No. 16/628,208, filed Jan. 2, 2020, which claims the benefit of International Application No. PCT/US2018/040902, filed Jul. 5, 2018, which claims the benefit of U.S. Provisional Application Ser. No. 62/529,269, filed Jul. 6, 2017, each of which is incorporated herein by reference in its entirety for all purposes.

FIELD OF THE INVENTION

The present disclosure is in the medical and biomedical field.

BACKGROUND OF THE DISCLOSURE

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Hot flushes are a major medical problem, which currently does not have a solution. Current treatments target skin vasodilation, as a part of the menopausal syndrome. Estrogen therapy is currently used to treat the entire menopausal syndrome in women. Estrogen therapy is not selective for hot flushes and has several dangerous side effects. Recently, a neurokinin-3 receptor antagonist has been tested in a clinical trial for treating menopausal hot flushes in a more specific manner, but its development has since been aborted due to hepatotoxicity. Thus there exists a need in the art for a selective therapy that targets hot flushes and lacks the side effects of estrogen therapy. There is also a need for at least one therapy that targets not necessarily skin vasodilation, but thermal discomfort—a major unpleasant symptom and cause of other symptoms in hot flushes.

SUMMARY OF THE DISCLOSURE

Various embodiments include a method for treating hot flushes in a subject, comprising: providing a composition comprising a transient receptor potential channel (TRP channel) blocker, or a pharmaceutical equivalent, analog, derivative, or salt thereof, and administering a therapeutically effective amount of the composition to the subject. In another embodiment, the TRP channel blocker is a TRP channel subfamily V member 1 (TRPV1) blocker, or a pharmaceutical equivalent, analog, derivative, or salt thereof. In another embodiment, the TRPV1 channel blocker has the structure:

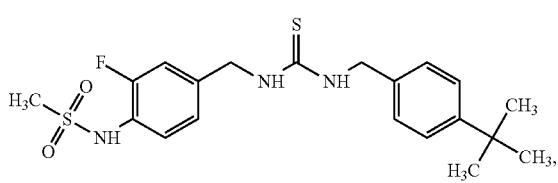

Formula (I)

or a pharmaceutical equivalent, analog, derivative, or salt thereof. In another embodiment, the TRPV1 channel blocker has the structure:

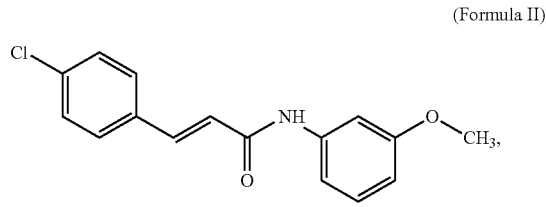 [SMILES: COc1cccc(NC(=O)/C=C/c2ccc(Cl)cc2)c1]

(Formula II)

or a pharmaceutical equivalent, analog, derivative, or salt thereof. In another embodiment, the TRPV1 channel blocker has the structure:

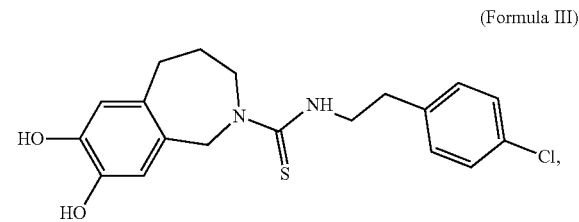 [SMILES: Oc1cc2c(cc1O)CN(C(=S)NCCc1ccc(Cl)cc1)CCC2]

(Formula III)

or a pharmaceutical equivalent, analog, derivative, or salt thereof. In another embodiment, the subject is female. In another embodiment, the subject is menopausal. In another embodiment, the subject is estrogen deficient. In another embodiment, the composition is a pellet, a tablet, a capsule, a solution, a suspension, a spray, an emulsion, an elixir, a gel, a cream, a patch, a plaster, a suppository, and/or a parenteral formulation. In another embodiment, treating hot flushes includes suppressing, inhibiting and/or reducing the risk of thermal discomfort. In another embodiment, the TRP channel blocker is listed in FIG. 5 herein. In another embodiment, the TRP channel blocker is listed in FIG. 6 herein. In another embodiment, the TRP channel blocker comprises capsazepine, A1165442, and/or SB366791. In another embodiment, the TRP channel blocker has the structure:

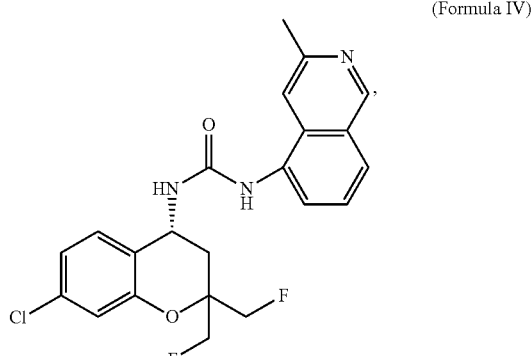

(Formula IV)

or a pharmaceutical equivalent, analog, derivative, or salt thereof. In another embodiment, the TRP channel blocker has the structure:

(Formula V)

or a pharmaceutical equivalent, analog, derivative, or salt thereof. In another embodiment, the composition is administered topically to the subject. In another embodiment, the composition is administered as a patch, plaster and/or spray.

Other embodiments include a method for amelioration, alleviation, or prevention of thermal discomfort associated with hot flushes in a subject, comprising selecting a subject in need of treatment for hot flushes, and administering to the subject a therapeutically effective amount of a transient receptor potential channel (TRP channel) blocker, or a pharmaceutical equivalent, analog, derivative, or salt thereof. In another embodiment, the TRP channel blocker is a TRP channel subfamily V member 1 (TRPV 1) blocker, or a pharmaceutical equivalent, analog, derivative, or salt thereof. In another embodiment, the TRP channel blocker has the structure:

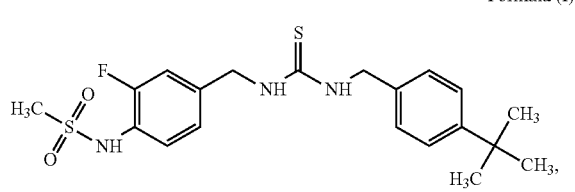

Formula (I)

or a pharmaceutical equivalent, analog, derivative, or salt thereof. In another embodiment, the TRP channel blocker has the structure:

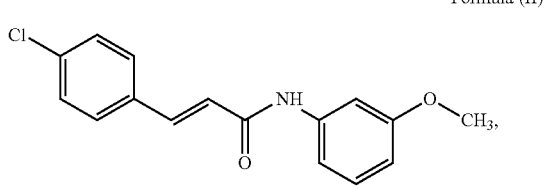

Formula (II)

or a pharmaceutical equivalent, analog, derivative, or salt thereof. In another embodiment, the TRP channel blocker has the structure:

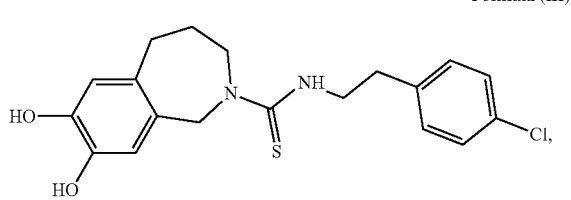

Formula (III)

or a pharmaceutical equivalent, analog, derivative, or salt thereof. In another embodiment, the subject is female. In another embodiment, the subject is menopausal. In another embodiment, the subject is estrogen deficient.

In another embodiment, the composition is a pellet, a tablet, a capsule, a solution, a suspension, a spray, an emulsion, an elixir, a gel, a cream, a patch, a plaster, a suppository or a parenteral formulation. In another embodiment, the TRP channel blocker comprises capsazepine, A1165442, and/or SB366791. In another embodiment, the TRP channel blocker has the structure:

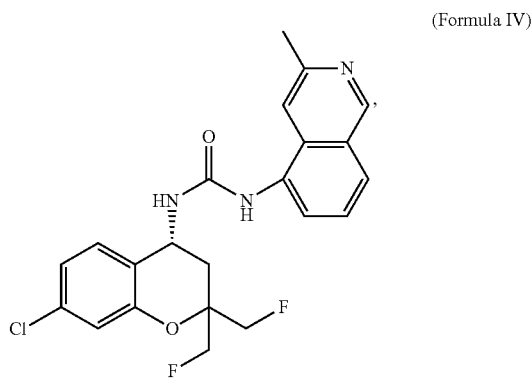 [SMILES: Cc1cc2c(NC(=O)N[C@@H]3CC(CF)(CF)Oc4cc(Cl)ccc43)cccc2cn1]

(Formula IV)

or a pharmaceutical equivalent, analog, derivative, or salt thereof. In another embodiment, the TRP channel blocker has the structure:

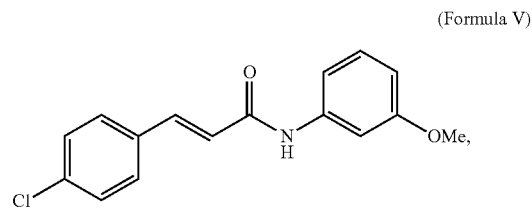 [SMILES: COc1cccc(NC(=O)/C=C/c2ccc(Cl)cc2)c1]

(Formula V)

or a pharmaceutical equivalent, analog, derivative, or salt thereof. In another embodiment, the TRP channel blocker is administered topically to the subject. In another embodiment, the TRP channel blocker is administered as a patch, plaster and/or spray.

Other features and advantages of the invention will become apparent from the following detailed description which illustrate, by way of example, various embodiments of the invention.

DESCRIPTION OF FIGURES

FIG. 5 depicts, in accordance with embodiments herein, a table listing various examples of TRPV1 antagonists. In various embodiments herein, one or more TRPV1 antagonists as described in FIG. 5 may be administered for treatment.

FIG. 6 depicts, in accordance with embodiments herein, a table listing various examples of TRPV1 antagonists that have no or mild hyperthermia effects when administered. In various embodiments herein, one or more TRPV1 antagonists as described in FIG. 6 may be administered for treatment.

DETAILED DESCRIPTION

Figure 1:
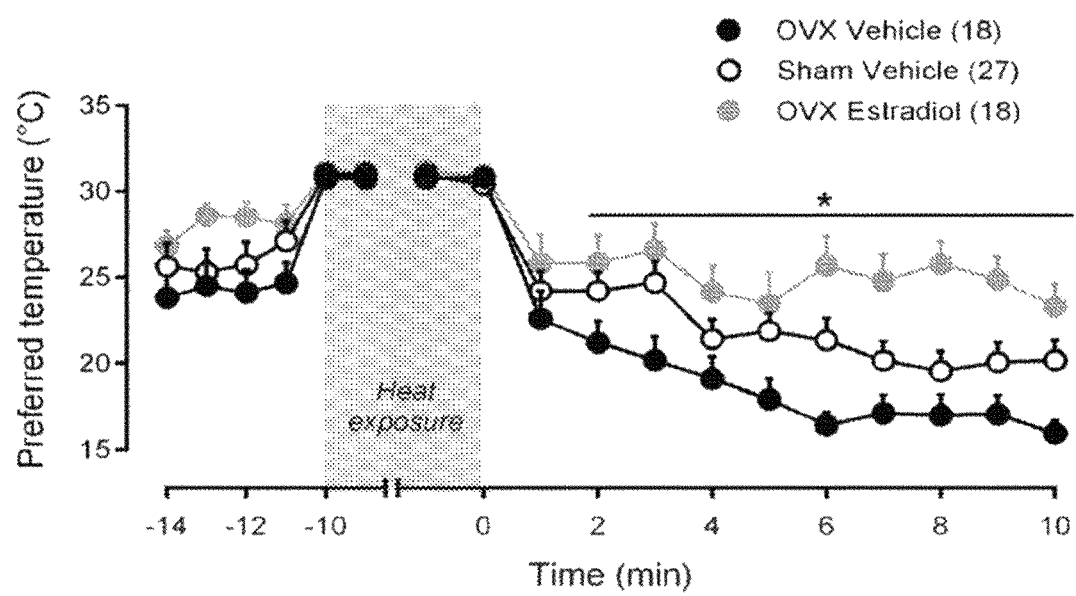
FIG. 1 depicts, in accordance with embodiments herein, preferred ambient temperature of the ovariectomized rats with estradiol replacement (OVX Estradiol), ovariectomized rats without estradiol replacement (OVX Vehicle), and sham-operated rats (Sham Vehicle) before and after a 10-min-long mild heat exposure (shaded area). The horizontal bar with an asterisk (*) denotes the time period corresponding to a significant difference in preferred ambient temperature between the OVX Vehicle and Sham Vehicle groups, as well as between the OVX Vehicle and OVX Estradiol groups ($P<0.05$).

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the term "topical application" refers to being applied to a surface such as skin.

As used herein the term "topically active" refers to the composition or medicament for topical application which treats predominately the surface on which it is applied.

As used herein, "treatment" or "treating" should be understood to include any indicia of success in the treatment, alleviation or amelioration of an injury, pathology or condition. This may include parameters such as abatement, remission, diminishing of symptoms, slowing in the rate of degeneration or decline, making the final point of degeneration less debilitating; improving a patient's physical or mental well-being; or, in some situations, preventing the onset of disease.

As used herein, the term "estrogen deficient" and "estrogen deficiency" refers to a low, zero, or reduced level of estrogen in a subject relative to a level found in a health individual.

As used herein, the terms "hot flash" or "hot flush" or "night sweats" refer to a sudden, unpleasant feeling of being hot (thermal discomfort), flushed skin, and/or sweating. Such hot flushes may be caused due to various reasons, such as but not limited to menopause, certain foods, as a side effect to prescription medicines, or diseases such as cancer.

As used herein, the terms "transient receptor potential channels" or "TRP channels" refer to a group of ion channels located mostly on the plasma membrane of numerous animal cell types. There are several types of TRP channels, such as TRPC ("C" for canonical), TRPV ("V" for vanilloid), TRPM ("M" for melastatin), TRPN, TRPA, TRPP ("P" for polycystic) and TRPML ("ML" for mucolipin), and the term "TRP channel" as used herein contemplates all such channels. As used herein, "TRP channel blocker" refers to a TRP channel antagonist.

As used herein, the terms "transient receptor potential cation channel subfamily V member 1" or "TRPV1" refers to an ion channel that has been implicated in mediation of multiple types of pain. TRPV1 is a protein in the TRP family which is encoded by the TRPV1 gene. TRPV1 is also sometimes referred to as the capsaicin receptor or the vanilloid receptor I. As used herein, "TRPV1 channel blocker" refers to a TRPV1 channel antagonist.

As described herein, in accordance with various embodiments herein, the present disclosure is directed towards compositions and methods for treatment, amelioration, and prevention of thermal discomfort that can be associated with hot flushes. In one embodiment, the inventor has invented a new treatment for the unpleasant sensations of being hot (thermal discomfort) in hot flushes rather than treating skin vasodilation. The inventor has used TRPV1 antagonists with certain pharmacological characteristics to treat the thermal discomfort associated with hot flushes. This novel treatment for hot flushes would benefit subjects who suffer from hot flushes. Instead of treating skin vasodilation, the inventors are treating the thermal discomfort, which is a major, if not only, cause of patients' complaints in hot flushes.

TRPV1 antagonists have been proposed as pain treatments, with multiple compounds being tested in clinical trials. However, administration of multiple TRPV1 antagonists resulted in hyperthermia in laboratory animals and human patients, a severe side effect that discouraged further development. Administration of some TRPV1 antagonists did not result in hyperthermia; it is believed that these TRPV1 antagonist compounds did not block the proton mode of channel activation. Although these compounds did not induce hypothermia, they also did not block the pain response to acid, and as such, their efficacy as analgesics was limited. Hence, the se TRPV1 antagonists with a limited pharmacological profile also have not been further developed.

As further described herein, those TRPV1 antagonists that potently block the proton mode of activation of the TRPV1 channel (most antagonists), cause hyperthermia. Because hyperthermia by itself is likely to provoke hot flushes, these antagonists have not been the preferred compounds of choice. However, in accordance with various embodiments herein, one may still be able use them if one can decrease or prevent the hyperthermic effect (e.g., by desensitization), or for example, by administering them in such a way that they do not cause hyperthermia (e.g., applying them topically to the skin), or for example, if their desired thermal discomfort-preventing effect compensates for the adverse hyperthermic effect. These antagonists could be referred to as "group A." In one embodiment, the present invention provides a method of treating hot flushes comprising providing a TRPV1 antagonist that potently blocks the proton mode of activation of the TRPV1 channel, and treating the subject by administering them in such a way that they decrease and/or prevent the hyperthermic effect.

Further, those antagonists that do not cause hyperthermia (they do not affect the protons mode of activation) can still be effective in preventing thermal discomfort, and in accordance with various embodiments herein, may be used to treat and/or prevent thermal discomfort and/or hot flushes. For example, as further disclosed herein and in accordance with embodiments herein, the inventors tested three such antagonists (namely, capsazepine, A1165442, and SB366791), and found that they successfully treated thermal discomfort. These antagonists could be referred to as "group B." In one embodiment, the present invention provides a method of treating hot flushes by providing a composition comprising one or more TRPV1 channel antagonists that do not affect the protons mode of activation, and administering a therapeutically effective dosage of the composition to the subject. In another embodiment, the present invention provides a method of treating hot flushes by providing a composition comprising capsazepine, A1165442, and/or SB366791, and administering a therapeutically effective dosage of the composition to the subject.

FIG. 6 herein shows antagonists from both aforementioned groups, group A and group B. For those that do not affect the protons mode of activation, FIG. 6 herein lists those that have been shown to cause only very mild hyperthermia, e.g., due to desensitization. In another embodiment, the present invention provides a composition comprising one or more antagonists described in FIG. 6 herein, and a pharmaceutical carrier. In another embodiment, the composition is formulated for topical administration to a subject for treatment of hot flushes.

As further disclosed herein, and in accordance with various embodiments, there are also antagonists that cause hypothermia (they potentiate the activation of TRPV1 by protons, instead of blocking it). Examples of such antagonists, as supported by animal studies, are A-1165901 and AMG7905. A priori, these antagonists can work very well in hot flushes by both blocking thermal discomfort (due to a blockade of the thermal mode of TRPV1 activation) and decreasing body temperature (by potentiating proton activation).

In one embodiment, the inventor has disclosed the novel use of certain TRPV1 antagonists (e.g., those TRPV1 antagonists that do not cause hyperthermia) to treat thermal discomfort in subjects with hot flushes. In some aspects, these compounds do not cause the most serious side effect of TRPV1 antagonists, hyperthermia. Because thermal discomfort of subjects with hot flushes is thermal in nature, the reduced efficacy of the compounds of interest against acid-induced pain is irrelevant and does not affect their ability to block any thermal signals, including those that trigger thermal discomfort. Both male and female subjects who suffer from hot flushes would benefit from this novel treatment. In one embodiment, the hot flushes may be menopausal. In another embodiment, the hot flushes may be caused by estrogen deficiency.

In one embodiment, the present disclosure provides a method for treating hot flushes, comprising administering to a subject a therapeutically effective amount of a composition comprising a transient receptor potential channel (TRP channel) blocker, or a pharmaceutical equivalent, analog, derivative, or salt thereof. In another embodiment, the present disclosure provides a method of suppressing or inhibiting thermal discomfort associated with hot flushes, comprising administering to a subject a therapeutically effective amount of a composition comprising a TRP channel blocker, or a pharmaceutical equivalent, analog, derivative, or salt thereof. In another embodiment, the present disclosure provides a method for amelioration, alleviation, and/or prevention of the uncomfortable sensation of being hot in hot flushes comprising, selecting a subject in need of treatment for hot flushes, and administering to the subject a therapeutically effective amount of a composition comprising a TRP channel blocker, or a pharmaceutical equivalent, analog, derivative, or salt thereof. In another embodiment, the present invention provides a method of treating, ameliorating, and/or preventing thermal discomfort, comprising administering to a subject a therapeutically effective amount of a composition comprising a TRP channel blocker, or a pharmaceutical equivalent, analog, derivative, or salt thereof. In some embodiments, the thermal discomfort may arise as a result of the subject experiencing a hormonal imbalance, such as a deficiency in levels of estrogen (i.e., compared to estrogen levels in a healthy subject).

In one embodiment, the hot flush is a result of menopause. In another embodiment, the hot flush is a result of low estrogen. In another embodiment, the hot flush is a result of the influence of spicy foods, caffeine, alcohol, or heat exposure. As readily apparent to one of skill in the art, hot flushes may be associated with a number of prescription drugs such as, but not limited to, Lupron (used for treatment of uterine fibroids), anti-hypertensives, anti-depressants, and anti-anxiety medications, and various embodiments herein may be used in conjunction with the subject receiving prescription drugs. In some embodiments, pancreatic tumors or other tumors in hormone-secreting organs may result in thermal discomfort from hot flushes. In some embodiments, hyperthyroidism or thyroid cancer may cause hot flushes. Other causes of hot flushes may be cancers such as lymphomas and leukemias, HIV infection, or tuberculosis.

In some embodiments, the TRP channel blocker is a TRP channel subfamily V member 1 (TRPV1) blocker or a pharmaceutically acceptable salt thereof. In one embodiment, the TRPV1 channel blocker has a structure depicted by formula (I), (II), or (III) or a pharmaceutically acceptable salt thereof.

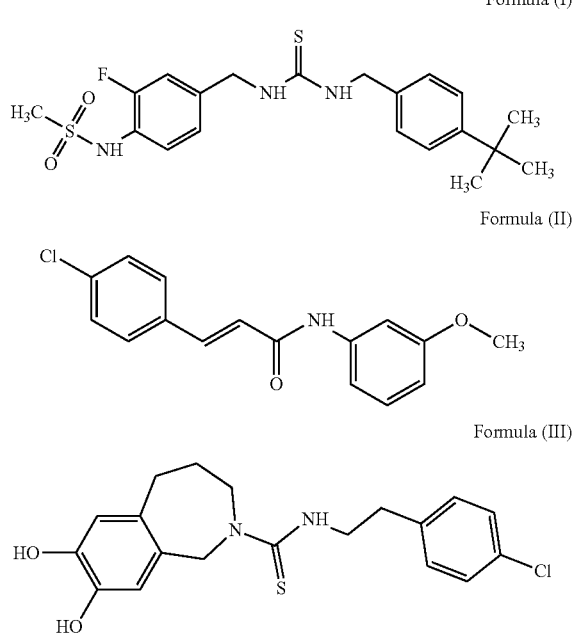

Formula (I)

Formula (II)

Formula (III)

In another embodiment, the TRP channel blocker has a structure depicted by Formula IV:

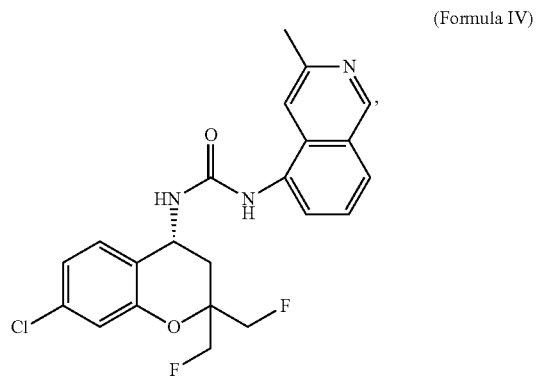 [SMILES: Cc1cc2c(NC(=O)N[C@@H]3CC(CF)(CF)Oc4cc(Cl)ccc43)cccc2cn1]

(Formula IV)

or a pharmaceutical equivalent, analog, derivative, or salt thereof.

In another embodiment, the TRP channel blocker has a structure depicted by Formula V:

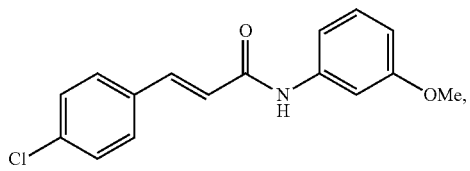

(Formula V)

or a pharmaceutical equivalent, analog, derivative, or salt thereof.

In one embodiment, the subject is female. In another embodiment the subject is male. In one embodiment, the subject is menopausal and/or is estrogen deficient. In one embodiment, the pharmaceutical composition is a pellet, a tablet, a capsule, a spray, a solution, a suspension, an emulsion, an elixir, a gel, a cream, a suppository or a parenteral formulation.

In another embodiment, the present invention provides a method of treating hot flushes by administering a therapeutically effective dosage of a composition comprising one or more TRPV1 antagonists described in FIGS. 5 and/or 6 herein.

In various embodiments, the present invention provides pharmaceutical compositions including a pharmaceutically acceptable excipient along with a therapeutically effective amount of one or more TRPV1 antagonists. For example, in one embodiment, the present invention provides a composition comprising one or more TRPV1 antagonists described in FIGS. 5 and/or 6 herein, and a pharmaceutically acceptable carrier, or excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intranasal, intradermal, intramuscular, intraperitoneal, intrapulmonary, intraspinal, intrastemal, intrathecal, intrauterine, intravenous, subarachnoid, subcapsular, subcutaneous, transmucosal, or transtracheal. Via the parenteral mute, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly.

Typical dosages of an effective composition comprising one or more TRPV1 antagonists can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied malignant tumors, or the responses observed in the appropriate animal models, as previously described.

The present invention is also directed to a kit to administering or preparing a composition comprising one or more TRPV1 antagonists. The kit is useful for practicing the inventive method of treating hot flushes, for example. The kit is an assemblage of materials or components, including at least one of the inventive compositions. Thus, in some embodiments the kit contains a composition including one or more compounds described in FIGS. 1 and/or 2, as described above.

The exact nature of the components configured in the inventive kit depends on its intended purpose. For example, some embodiments are configured for the purpose of treating hot flushes. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to administer a composition comprising one or more TRPV1 antagonists. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing one or more TRPV1 antagonists. The packaging material generally has an external label which indicates the contents and/or purpose of the kit and/or its components.

In accordance with various embodiments herein, the active agent in topical formulation comprises one or more TRPV1 antagonists. In some embodiments, the active agent can be either capsazepine, A1165442, or SB36679, or a combination thereof. The concentration of the active agent in the topical formulation may range from about 0.1-30% (w/w). For example, the active agent may comprise about 0.1-5%, 0.5-3%, 1-2%, 1-3%, 2-10%, 5-10%, 5-15%, 1015%, 15-20%, 10-20%, 20-25%, 15-30%, 20-30%, 10-30%, or 25-30% (why) of the topical formulation. In accordance with various embodiments herein, the concentration of the active agent in the topical formulation described herein refers to the percentage of the total weight of the active agent in dry form of the total weight of the topical formulation as a whole.

In some embodiments, the topical formulation of the invention may further comprise one or more emollients, fragrances, or pigments. In accordance with various embodiments herein, the formulation may also further contain thickening agents, wetting agents, fillers, preservatives, cross-linking agents, surfactants, and/or stabilizers, for example.

In some embodiments, the topical formulation may be, or include, an ointment base. Or, for example, the ointment base may be a cream base. In one embodiment, for example, the topical formulation may include one or more TRPV1 antagonists, and include a cream base where the cream base may contain more than 20% water and volatiles and/or typically contain less than 50% hydrocarbons, waxes, or polyols as the vehicle for the drug substance. The cream base can be a multiphase preparation containing a lipophilic phase and an aqueous phase. In some instances, the cream base is a lipophilic cream base, which has a lipophilic phase as the continuous phase. Such a cream base may contain water-in-oil emulsifying agents such as wool alcohols, sorbitan esters and monoglycerides. In other instances, the cream base may be a hydrophilic cream base, which has an aqueous phase as the continuous phase. Such a cream base may contain oil-in-water emulsifying agents such as sodium or trolamine soaps, sulfated fatty alcohols, polysorbates and polyoxyl fatty acid and fatty alcohol esters, which may be in combination with water-in-oil emulsifying agents, if needed.

In accordance with various embodiments herein, the present invention provides a composition that may be used for a topical plaster application. For example, in one embodiment, a composition that includes capsazepine, A1165442, and/or SB36679 may be formulated as a plaster for topical application to a subject.

In another embodiment, a topical application may include a patch formulation. For example, such patches for topical application at the site of action may generally consist of a drug-containing self-adhesive so-called matrix layer, an often textile backing layer and a protective layer to be removed before use for the matrix.

In accordance with various embodiments herein skin compatibility can also play an important role in the topical systems, wherein only good skin-compatible ingredients for the matrix can be made of such patches, and beyond the adhesive behavior must be so excluded considered that on the one hand, the patch over the intended time of application glued reliably and on the other hand, when removing the patch no excessive mechanical irritation the skin takes place.

Additionally, the patch must be able to deliver sufficient drug to reach in the tissues underlying the patches, i.e., the site of action, sufficiently high tissue levels. Also, the requirement for a sufficient stability of the dosage form with respect to the active ingredient content, of the release of active agent and the adhesive performance.

In one embodiment, the present invention includes a topical, medicinal spray composition. For example, in one embodiment, the present invention provides a composition that includes one or more TRPV1 antagonists, formulated to be applied to a subject as a topical, medicinal spray. In another embodiment, the one or more TRPV1 antagonists include capsazepine, A1165442, and/or SB36679. In one embodiment, the composition comprises a drug or combination of drugs as a solution or suspension in a vehicle optionally containing a polymer or combination of polymers which, when sprayed on the surface of the skin, forms a film on the skin. The compositions of the invention preferably comprise up to about 30% of at least one medicament (e.g., 0.0001% to about 30%), more preferably up to about 10% of at least one medicament (e.g., 0.0001% to about 10%) and most preferably up to about 5% of at least one medicament (e.g., 0.0001% to about 5%) dissolved or suspended in one or more vehicles which comprise up to 90% of the composition (e.g., 0.0001% to about 90%). The composition may further contain one or more film former, solubilizer, permeation enhancer and plasticizer. The composition may contain one or more of these additives in amounts of up to about 10% film-former (e.g., 0.0001% to about 10%), up to about 10% solubilizer (e.g., 0.0001% to about 10%), up to about 8% permeation enhancer (e.g., 0.0001% to about 8%), and up to about 10% plasticizer (e.g., 0.0001% to about 10%). The inventive composition may be sprayed on a topical site to form a stable, breathable film on the site, from which film the medicaments act locally on the surface or are transdermally available. Preferably, the composition further comprises up to about 7% (w/w) of one or more water-soluble additives (e.g., 0.0001% to about 7%). The drug or combination of drugs so deposited in the matrix of the film-former may remain solubilized or suspended. The exact formulation of the composition may vary depending on the nature of the particular medicament used (for example, the solubility profile) and the release profile desired. The compositions can be dispensed from any dispenser, preferably a dispenser which provides the composition as a spray, and may be used for systemic action or topical action. The drug from the composition may be released over a period of time or immediately.

The compositions of the present invention are preferably applied in a metered dose over a predetermined surface area. Accordingly, the present invention may also provide for the administration of the composition by spraying the composition from a dispenser. The invention further provides a method for applying the composition and the resultant film.

Preferably, the composition is dispensed from a pump dispenser or from an aerosol dispenser. In the latter case, the composition additionally comprises from about 10% to 90% of propellant in order to provide a suitable pressure within the aerosol dispenser. Generally, propellant is not required for compositions dispensed from a pump dispenser. However, if desired, such compositions may also comprise from about 10% to 90% of a propellant which is liquid at room temperature.

In another embodiment, the present invention may also provide a method of preparing a pump dispenser containing the spray composition of the invention comprising mixing the ingredients of the composition with or without liquid propellant and placing the mixed ingredients in a pump dispenser.

In addition, in another embodiment, the present invention provides a method of preparing an aerosol dispenser containing the spray composition of the invention comprising mixing the ingredients of the composition without propellant and charging the mixture together with propellant into an aerosol dispenser. The composition is preferably dispensed from the chosen dispenser in a metered dose.

The medicament can be any medicinal compound in the salt or base form or a combination of compounds which is stable on mixing with the other ingredients of the composition and effective on topical administration.

Embodiments of the present disclosure are further described in the following examples. The examples are merely illustrative and do not in any way limit the scope of the invention as claimed.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

Hot flushes (or hot flashes) constitute the most frequent complaint of postmenopausal women. There are no treatments for hot flushes other than the estrogen treatment, which treats the entire postmenopausal syndrome. Contrary to current beliefs, the inventors have disclosed that abnormal thermal discomfort is involved in this disorder.

Many TRPV1 antagonists have been synthesized and tested by multiple pharmaceutical companies as potential painkillers, but they have not been developed further due to the dangerous side effect—hyperthermia. The TRPV1 antagonist compounds that do not cause hyperthermia have reduced analgesic efficacy, as they do not block the proton mode of TRPV1 activation. Hence for inflammatory pain, these compounds would not work. In one embodiment, the inventors have disclosed that they do, however, block the heat mode. As such, TRPV1 antagonists are potential drugs to treat the abnormal heat discomfort, which takes place in hot flushes. Many such compounds—designed, synthesized, and thoroughly tested—are now stored by pharmaceutical companies all over the world, but they have no use. The present disclosure presents a novel use of these compounds, for the treatment of thermal discomfort associated with hot flushes.

TRPV1 antagonists have been proposed as pain treatments, with multiple compounds being tested in clinical trials. However, administration of multiple 'TRPV1 antagonists resulted in hyperthermia in laboratory animals and human patients, a severe side effect that discouraged further development. Administration of some TRPV1 antagonists did not result in hyperthermia; it is believed that these TRPV1 antagonist compounds did not block the proton mode of channel activation. Although these compounds did not induce hypothermia, they also did not block the pain response to acid, and as such, their efficacy as analgesics was limited. Hence, these TRPV1 antagonists with a limited pharmacological profile also have not been further developed.

Example 2

The TRPV1 Antagonists "Paradox"—Explained

As noted above and known to those of skill in the art, those TRPV1 antagonists that potently block the proton mode of activation of the TRPV1 channel (most antagonists), cause hyperthermia. Because hyperthermia by itself is likely to provoke hot flushes, these antagonists have not been the preferred compounds of choice. However, in accordance with various embodiments herein, one may still be able use them if one can decrease or prevent the hyperthermic effect (e.g., by desensitization), or for example, by administering them in such a way that they do not cause hyperthermia (e.g., applying them topically to the skin), or for example, if their desired thermal discomfort-preventing effect compensates for the adverse hyperthermic effect. These antagonists could be referred to herein as "group A."

Further, those antagonists that do not cause hyperthermia (they do not affect the protons mode of activation) can still be effective in preventing thermal discomfort, and in accordance with various embodiments herein, may be used to treat and/or prevent thermal discomfort and/or hot flushes. For example, as further disclosed herein and in accordance with embodiments herein, the inventors tested three such antagonists (namely, capsazepine, A1165442, and SB366791), and found that they successfully treated thermal discomfort. These antagonists could be referred to herein as "group B."

FIG. 6 herein shows antagonists from both aforementioned groups, group A and group B. For those that do not affect the protons mode of activation, FIG. 6 herein lists those that have been shown to cause only very mild hyperthermia, e.g., due to desensitization.

As further disclosed herein, and in accordance with various embodiments, there are also antagonists that cause hypothermia (they potentiate the activation of. TRPV1 by protons, instead of blocking it). Examples of such antagonists, as supported by animal studies, are A1165901 and AMG7905. A priori, these antagonists can work very well in hot flushes by both blocking thermal discomfort (due to a blockade of the thermal mode of TRPV1 activation) and decreasing body temperature (by potentiating proton activation).

Example 3

Experiments

Hot flushes are currently viewed as a normal reaction of abnormal (readily occurring) skin vasodilation. However, similar vasodilation often develops in non-estrogen-deficient individuals, both men and women, under many circumstances, such as, in a warm environment, after cold exposure, after eating spicy food, during heavy lifting, during sexual intercourse, when a person is ashamed or angry, and myriad other conditions. In some embodiments, the unpleasant general feeling of being hot (thermal discomfort) may be associated with hot flushes.

Thermal sensations are mediated by Thermo-TRP channels. There are six main warmth-sensitive channels in the skin and neurons that innervate the skin: TRPV1, TRPV2, TRPV3, and TRPV4, TRPM2, and TRPM3. TRPV1 channel is abundant on pain fibers and has a temperature threshold around 41° C. in vitro, but there is strong evidence that in vivo the
threshold is lower, and that many biologically active substances can affect this threshold. In one embodiment, estrogen depletion/deficiency results in a TRPV1-mediated increase in the thermal pain in the skin and also in the general feeling of thermal discomfort. TRPV1 is activated by temperature, protons, or capsaicin (Garami A, et al. J Neurosci 30: 1435-1440, 2010). Activation by temperature is critical for thermal discomfort.

These findings constitute the basis for promoting the thermally neutral TRPV1 antagonists (i.e., TRPV1 antagonists that do not induce hyperthermia or hypothermia), those TRPV1 antagonists that do not block the proton mode of activation, and thus do not cause hyperthermia, but block the thermal mode, as a new drug for treating hot flushes.

Example 4

TRPV1 Antagonists Abolish Thermal Discomfort Characteristic of Hot Flushes and Related Postmenopausal Symptoms—Methods

Animals

Experiments were performed in adult female Wistar rats (Envigo) weighting 240-280 g at the day of the first surgery (Day 0). Rats were housed three per cage in standard "show boxes". The room was maintained on a 12:12 h light-dark cycle (lights-on at 6 AM) at 24±2° C. All protocols were approved by the Institutional Animal Care and Use Committee.

Protocols

On Day 0, each rat was subjected to a bilateral ovariectomy or sham surgery, either with or without simultaneous implantation of a miniature data logger into the peritoneal cavity for body temperature measurement. On Day 7, the ovariectomized rats were implanted subcutaneously with a capsule containing either estradiol or vehicle, and the sham-operated rats were implanted with a capsule containing vehicle. On Days 6-15, the rats were habituated to experimental setups and procedures. The rats were taken into experiments between Days 16 and 20 (Experiments 1-3) or on Days 13 and 20 (Experiment 4); each rat was used in two experiments. Thermal discomfort was studied in one of two tests: the ambient warming-induced cold-seeking test in a thermogradient apparatus (cold-seeking test; Experiments 1-3) or the internal warming-induced cessation of warm sucrose intake test (sucrose intake cessation test; Experiment 4). Some ovariectomized rats were treated with a TRPV1. antagonist (capsazepine, Al 165442, or SB366791) or vehicle prior to a test. After experiments (Day 21), each rat used in Experiments 1-3 was euthanized, and the uterus was removed and weighed to confirm the completeness of the ovariectomy and the effectiveness of the estradiol replacement procedure.

Experiments

The goal of Experiment 1 was to determine whether ovariectomy facilitates the cold-seeking behavior after heat exposure, and whether this facilitation (if it occurs) is estradiol-dependent. The following groups of rats were studied: OVX Vehicle (ovariectomized rats that received vehicle via an implanted capsule); Sham Vehicle (sham-operated rats that received vehicle via a capsule); and OVX Estradiol (ovariectomized rats that received estradiol via a capsule).

The goal of Experiment 2 was to determine whether capsazepine attenuates the development of the exaggerated cold-seeking behavior in ovariectomized rats. Rats assigned to this experiment were treated with capsazepine or its vehicle by oral gavage 30 min prior to the heat exposure. The following groups of rats were studied: OVX Vehicle+Capsazepine (ovariectomized rats that received vehicle via an implanted capsule and were pretreated with capsazepine by oral gavage); OVX Vehicle+Vehicle (ovariectomized rats that received vehicle via a capsule and were pretreated with vehicle by gavage); and OVX Estradiol+Vehicle (ovariectomized rats that received estradiol via a capsule and were pretreated with vehicle by gavage).

The goal of Experiment 3 was to determine whether A1165442 attenuates the development of the exaggerated cold-seeking behavior caused by ovariectomy. This experiment was performed exactly as Experiment 2, except that rats were pretreated with A1165442 instead of capsazepine.

The goal of Experiment 4 was to determine whether ovariectomized, heat-exposed rats decrease the consumption of sucrose solution when placed in a warm environment (40° C.) compared to a cool environment (27° C.), and whether this decrease is estradiol-dependent and can be attenuated by SB366791. Rats were treated with SB366791 or its vehicle by oral gavage 20 min prior to the heat exposure. The following groups were studied: OVX Vehicle+SB366791 (ovariectomized rats that received vehicle via an implanted capsule and were pretreated with SB366791 by oral gavage); OVX Vehicle-I-Vehicle (ovariectomized rats that received vehicle via a capsule and were pretreated with vehicle by gavage); and OVX Estradiol+Vehicle (ovariectomized rats that received estradiol via a capsule and were pretreated with vehicle by gavage).

Surgeries

Ovariectomy and data logger implantation. The ovariectomy was performed under anesthesia with a mixture of ketamine (55.6 nig/kg), acepromazine maleate (1.1 mg/kg), and xylazine (5.6 mg/kg), injected intraperitoneally. The antibiotic protection was provided by intramuscular enrofloxacin (1.1 mg/kg). Buprenorphine (50 µg/kg) was administered subcutaneously for postsurgical analgesia. Laparotomy (in the upper half of the flank) was performed on the left side first, and the left ovary was exposed by pulling out the periovarian fat pad. The oviduct with its surrounding tissue was ligated and cut distal to the ligature. The ovary was removed, and the uterine horn was returned into the peritoneal cavity. The surgical wound was closed in layers: the peritoneum and muscle first followed by the skin. The same surgical procedure was conducted on the right side to remove the right ovary. For sham ovariectomy, the same procedure was performed bilaterally, except that the oviduct was not ligated or cut, and the ovary was not removed.

Fstradiol capsule implantation. For hormone replacement, two 20-mm-long silastic capsules (Dow Corning) containing 1.7-estradiol (Sigma Aldrich; 180 µg/mL. in sesame oil) or sesame oil were implanted subcutaneously through a small incision in the interscapular region, under isofluorane (3%) anesthesia.

Tests

Cold-seeking test. A rat was placed in a channel of a thermogradient apparatus and allowed to move freely, thus, selecting its preferred ambient temperature, for 2 h. Thereafter, the rat was subjected to a mild heat exposure, during which the rat was locked in a warm region of the apparatus (31° C.) for 10 min. After the restricting device was removed, the rat was allowed to move freely again and select its preferred thermal environment. The preferred ambient temperature was recorded for 10 min.

Sucrose intake cessation test. On the day of the test, rats in their individual cages were placed in an environmental chamber and exposed to heat (32.5° C.) for 10 minutes. A 0.1-ml-graded glass burette thermally insulated with a gel sleeve was introduced to each cage. Each burette was fitted with a stainless steel spout and filled with a 0.3 M sucrose solution at either 27 or 40° C., and sucrose solution consumption was recorded for 15 min.

Drugs and Drug Administration

Three TRPV1 antagonists were tested: capsazepine (Cayman Chemical; 40 mg/kg, Experiment 2), A1165442 (MedChem Express; 100 mg/kg, Experiments 3), and SB366791 (Tocris Bioscience; 10 mg/kg, Experiment 4). All compounds were dissolved in a solution containing 30% of propylene glycol and 30% ethanol in either saline (capsazepine) or water (A1165442 and SB366791). Working solutions were prepared immediately before experiments at the following concentrations: 40 mg/ml (capsazepine), 100 mg/ml (A1165442), and 10 mg/ml (SB366791). All compounds and their vehicles were administered per os (by oral gavage, 0.1 ml/kg).

Thermogradient Apparatus

The thermogradient apparatus used is described elsewhere (Almeida et al., 2006; Wanner et al., 2017). Briefly, the apparatus consists of six 200-cm-long aluminum channels. At each end, all channels share a common aluminum wall, which separates the channels from a large tank; the tank at the "warm" end of the channels is filled with water heated by two electric units (PolyScience) to maintain air temperature inside the channels at this end at 36.0° C. The tank at the "cold" end is constantly perfused with 10% ethylene glycol by an external-circulation cooling/heating pump (PolyScience) to maintain air temperature inside the channels at this end at 14.0° C. In this setting, all channels have a common, nearly linear longitudinal temperature gradient of 0.1° C./cm. Rats are placed in the apparatus, one rat per channel, and they freely move inside their channels to select their preferred ambient temperature. The position of each rat is tracked by a video camera (Panasonic Model WV-CP280, Matsushita Electric Industrial), and the ambient temperature is recorded in multiple points by thermocouples connected to a multichannel temperature data acquisition system (Omega TempScan). Position data are converted into preferred ambient temperature data using a linear regression equation obtained from temperatures measured by thermocouples and thermocouple positions.

Data Analysis

All data are expressed as mean±SE. The preferred ambient temperature and sucrose intake data analyzed by a two-way repeated-measurements ANOVA, followed by the Fisher or Newman-Keuls multiple comparisons test, as appropriate. The uterus mass data were analyzed by a one-way ANOVA followed by the Fisher test. The significance level was set at $P=0.05$.

Example 5

TRPV1 Antagonists Abolish Thermal Discomfort Characteristic of Hot Flushes and Related Postmenopausal Symptoms Results In Experiment 1, following mild heat exposure, ovariectomized rats expressed significantly stronger cold-seeking behavior than sham rats (FIG. 1), thus, demonstrating that, following ovariectomy, rats more readily develop thermal discomfort after a mild heat exposure and try to cool themselves by moving toward a cooler environment. Estradiol blocks this effect (FIG. 1), thus, showing that the increased propensity for cold seeking in ovariectomized rats is estradiol-dependent. The completeness of ovariectotny and effectiveness of the estradiol replacement procedure were confirmed by the uterus mass data: ovariectomy decreased the mass to 0.13±0.01 g as compared to 0.40±0.02 g in sham rats ($P<0.001$), whereas the estradiol replacement restored the uterus mass of ovariectomized rats to 0.42±0.02 g ($P<0.001$).

Figure 2:
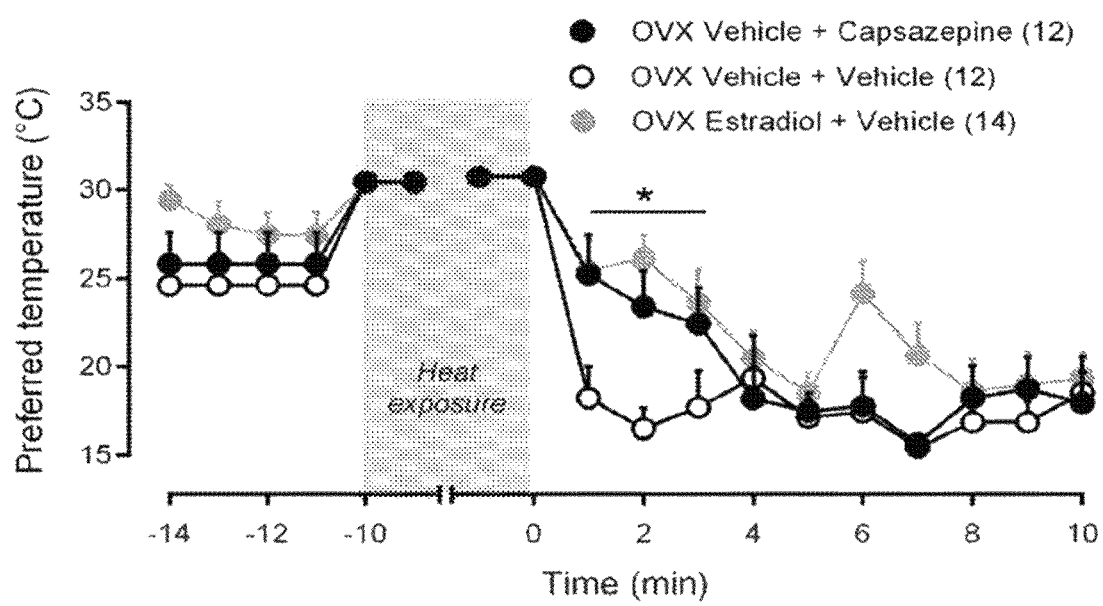
FIG. 2 depicts, in accordance with embodiments herein, preferred ambient temperature of ovariectomized rats with capsazepine pretreatment (OVX Vehicle+Capsazepine) and without capsazepine pretreatment (OVX Vehicle+Vehicle), as well as of ovariectomized rats with estradiol replacement (OVX Estradiol+Vehicle) before and after a 10-min-long mild heat exposure (shaded area). The horizontal bar with an asterisk (*) denotes the time period corresponding to a significant difference in the preferred ambient temperature between the OVX Vehicle+Capsazepine and OVX Vehicle+Vehicle groups, as well as between the OVX Vehicle+Vehicle and OVX Estradiol+Vehicle groups (P<0.05).
Figure 3:
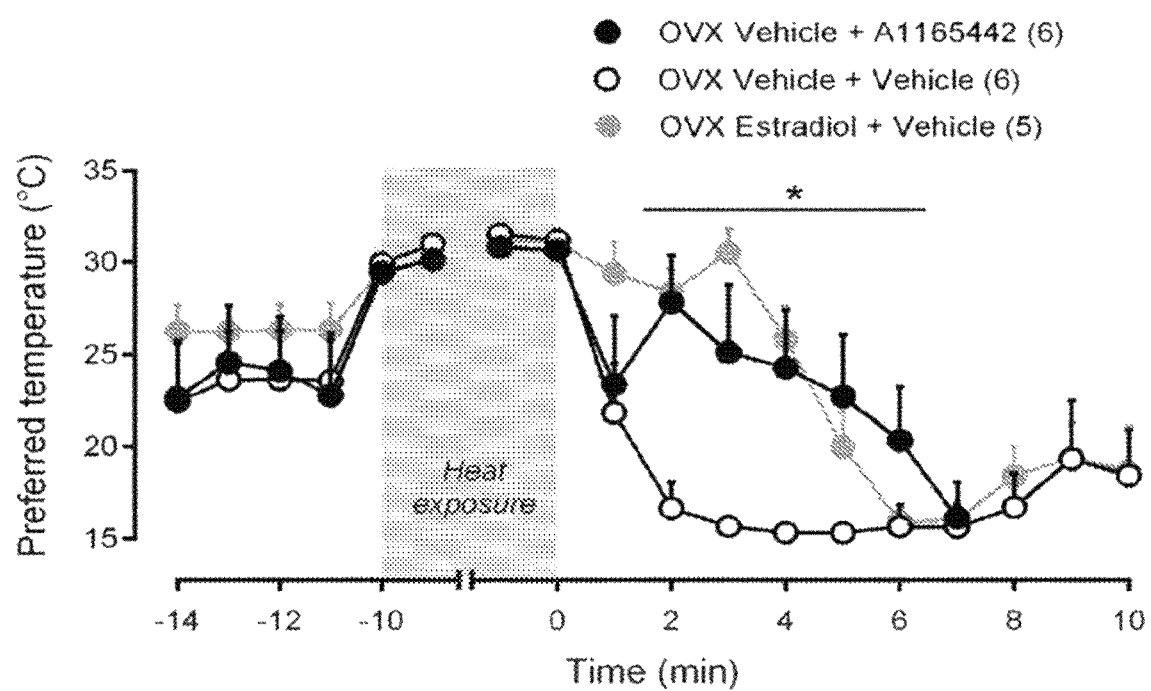
FIG. 3 depicts, in accordance with embodiments herein, preferred ambient temperature of ovariectomized rats with A1165442 pretreatment (OVX Vehicle+A1165442) and without A1165442 pretreatment (OVX Vehicle+Vehicle), as well as of the ovariectomized rats with estradiol replacement (OVX Estradiol+Vehicle) before and after a 10-min-long mild heat exposure (shaded area). The horizontal bar with an asterisk (*) denotes the time period corresponding to a significant difference in the preferred ambient temperature between the OVX Vehicle+A 1165442 and OVX Vehicle+Vehicle groups, as well as between the OVX Vehicle+Vehicle and OVX Estradiol+Vehicle groups (P<0.05).

In Experiment 2 (FIG. 2) and Experiment 3 (FIG. 3), the TRPV1 antagonists (capsazepine and A1165442. respectively) strongly attenuated the heat exposure-induced cold-seeking behavior in ovariectomized rats. These data demonstrate that thermal discomfort that is readily provoked in ovariectomized rats by mild heat exposure is treated/attenuated by TRPV1 antagonists. The completeness of ovariectomy and effectiveness of the estradiol replacement procedure were confirmed by the uterus mass data (not shown).

Figure 4:
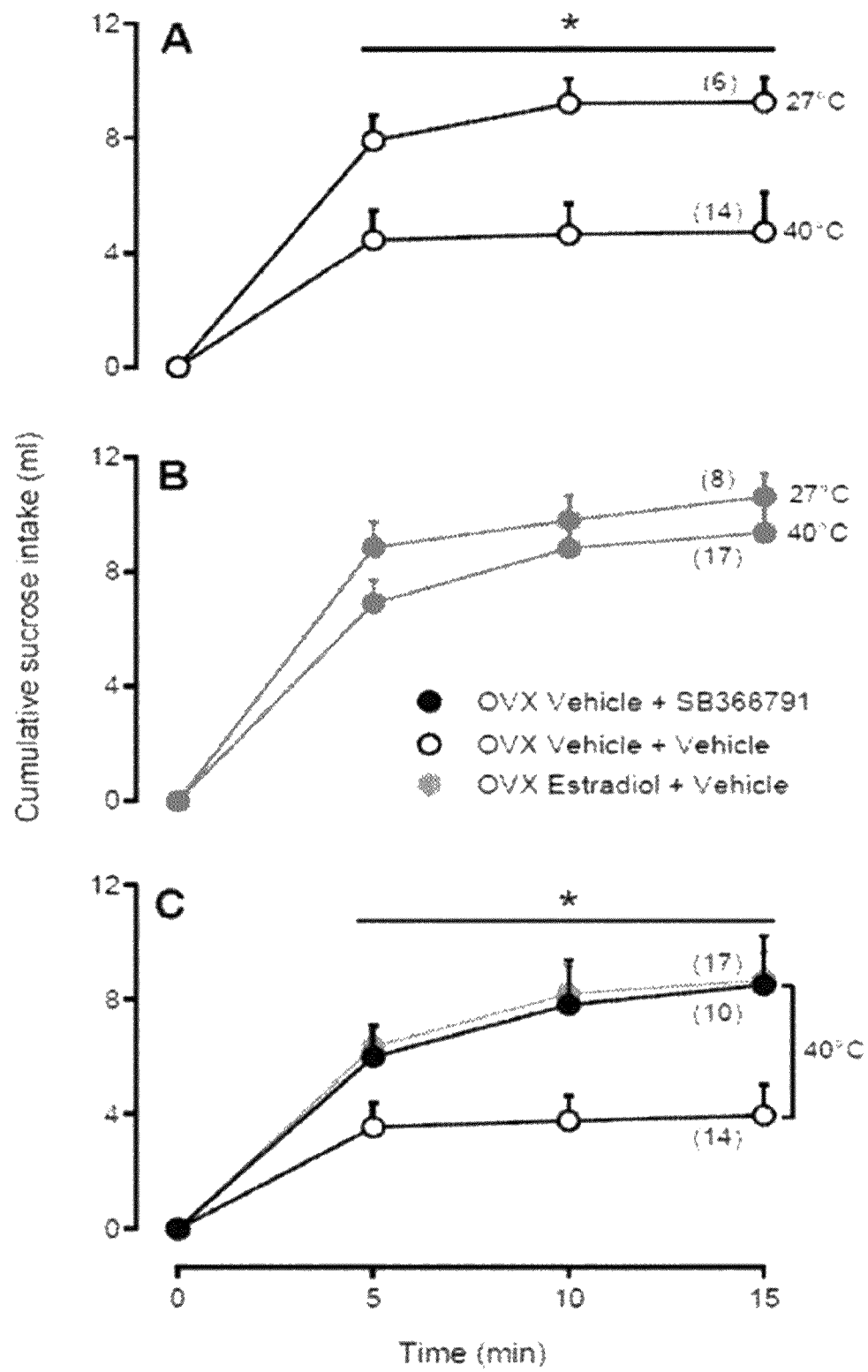
FIG. 4 depicts, in accordance with embodiments herein, tables referring to experimental results. A: Cumulative intake of a cool (27° C.) or warm (40° C.) sucrose solution by ovariectomized rats without estradiol replacement (OVX Vehicle+Vehicle) immediately after a mild heat exposure. The horizontal bar with an asterisk (*) denotes the time period corresponding to a significant difference between the intake of sucrose solution of different temperatures (P<0.05). B: Cumulative intake of a cool or warm sucrose solution by ovariectomized rats with estradiol replacement (OVX Vehicle+Estradiol) immediately after a mild heat exposure. C: Cumulative intake of a warm sucrose solution by ovariectomized rats with SB366791 pretreatment (OVX Vehicle+SB366791) or without SB366791 pretreatment (OVX Vehicle+Vehicle), as well as of the ovariectomized rats with estradiol replacement (OVX Vehicle-I-Estradiol). The horizontal bar with an asterisk (*) denotes the time period corresponding to a significant difference between the intake of the warm sucrose solution between the OVX Vehicle+SB366791 and OVX Vehicle+Vehicle groups, as well as between the OVX Vehicle+Vehicle and OVX Estradiol+Vehicle groups (P<0.05). In all panels, a number in parentheses is the number of animals in the corresponding group.

In Experiment 4, following a mild heat exposure, ovariectomized rats without estradiol replacement (FIG. 4, panel A) consumed significantly less sucrose when the sucrose solution was warm (40° C.), compared to when the sucrose solution was cool (27° C.). These data demonstrate that ovariectomized rats tried to avoid thermal discomfort by limiting the sucrose consumption when the consumption was associated with internal body warming. Estradiol replacement (FIG. 4, panel B) strongly attenuated this warming-avoidance effect: following the same heat exposure, estradiol-treated ovariectomized rats did not significantly decrease the amount of sucrose solution consumed when the temperature of the solution was increased from 27 to 40° C. These data demonstrate that the avoidance of internal warming induced by a mild heat exposure in ovariectomized rats is estradiol-dependent and can be attenuated by the TRPV1 antagonist used in this experiment (SB366791, FIG. 4, panel C).

Cumulatively, these data demonstrate that mild heat exposure causes thermal discomfort in ovariectomized rats, which expresses itself in an active search for a colder environment and in avoidance of internal warming. This discomfort is estradiol-dependent—a feature characteristic of hot flushes and related postmenopausal symptoms. TRPV1 antagonists (capsazepine, A1165442, and SB366791) treat this thermal discomfort.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about."

Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein.

Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:
1. A method for treating thermal discomfort associated with hot flushes in a subject in need thereof, comprising:
administering a therapeutically effective amount of a composition to the subject, wherein the composition comprises a transient receptor potential subfamily V member 1 channel (TRPV1 channel) antagonist having a structure of

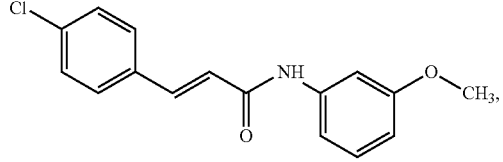

Formula II

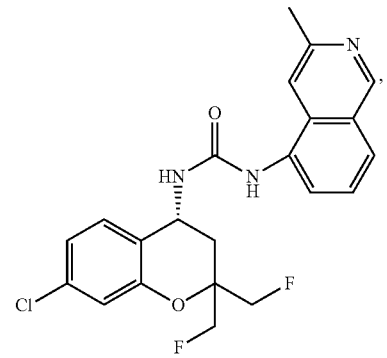

(Formula IV)

or a salt thereof; and wherein the therapeutically effective amount comprises the amount effective in suppressing, ameliorating, alleviating, and/or preventing the thermal discomfort in the subject, while not impacting vasodilation.

2. The method of claim 1, wherein the subject is female.

3. The method of claim 1, wherein the subject is menopausal.

4. The method of claim 1, wherein the subject is estrogen deficient.

5. The method of claim 1, wherein the composition is a pellet, a tablet, a capsule, a solution, a suspension, a spray, an emulsion, an elixir, a gel, a cream, a patch, a plaster, a suppository, or a parenteral formulation.

6. The method of claim 1, wherein the therapeutically effective amount comprises the amount effective in suppressing the thermal discomfort.

7. The method of claim 1, wherein the composition is administered topically to the subject.

8. The method of claim 1, wherein the composition is administered as a patch, plaster and/or spray.

9. A method for suppression, amelioration, alleviation, or prevention of thermal discomfort associated with hot flushes in a subject in need thereof, comprising:

selecting the subject in need of treatment for hot flushes; and administering to the subject a therapeutically effective amount of a transient receptor potential subfamily V member 1 channel (TRPV1 channel) antagonist having the structure of Formula (II)

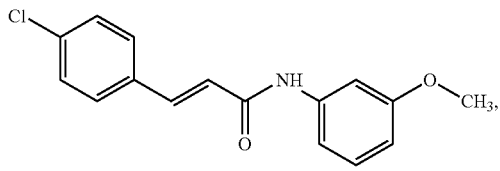

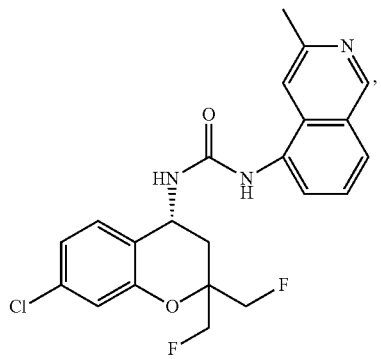

(Formula IV)

or a salt thereof; and wherein the administration does not impact vasodilation of the subject.

10. The method of claim 9, wherein the subject is female.

11. The method of claim 9, wherein the subject is menopausal.

12. The method of claim 9, wherein the subject is estrogen deficient.

13. The method of claim 9, wherein the TRPV1 channel antagonist is part of a pellet, a tablet, a capsule, a solution, a suspension, an emulsion, an elixir, a gel, a cream, a suppository or a parenteral formulation.

14. The method of claim 9, wherein the TRPV1 channel antagonist is administered topically to the subject.

15. The method of claim 9, wherein the TRPV1 channel antagonist is administered as a patch, plaster and/or spray.

16. The method of claim 1, wherein the thermal discomfort is estradiol-dependent.

17. The method of claim 1, wherein the thermal discomfort is associated with menopausal hot flushes.

\* \* \* \* \*